(12) United States Patent
Dean (10) Patent No.: US 6,306,111 B1
(45) Date of Patent: Oct. 23, 2001

(54) REHABILITATIVE SHOULDER SUPPORT

(76) Inventor: Joetta G. Dean, 2 Park Ave., Fair Haven, VT (US) 05743

(*) Notice: Subject to any disclaimer, the term of this patent is extended or adjusted under 35 U.S.C. 154(b) by 0 days.

(21) Appl. No.: 09/614,020

(22) Filed: Jul. 11, 2000

(51) Int. Cl.[7] .............................. A61F 5/00; A61F 13/00
(52) U.S. Cl. .................................. 602/20; 602/4; 602/62; 128/DIG. 19
(58) Field of Search ............................... 602/4, 5, 19–20, 602/60–63; 128/846, 869, 873–875, DIG. 19; 2/44, 45

(56) References Cited

U.S. PATENT DOCUMENTS

| 50,128 | * | 9/1865 | Hudson . | |
|---|---|---|---|---|
| 195,941 | * | 10/1877 | McCabe . | |
| 3,906,944 | * | 9/1975 | Christen | 128/133 |
| 4,735,198 | * | 4/1988 | Sawa | 128/133 |
| 4,947,870 | * | 8/1990 | Larcher | 128/875 |
| 5,105,828 | * | 4/1992 | Grant | 128/876 |
| 5,163,450 | * | 11/1992 | Cadichon et al. | 128/784 |
| 5,628,725 | * | 5/1997 | Ostergard | 602/62 |
| 5,857,990 | * | 1/1999 | Maas | 602/62 |
| 6,106,493 | * | 8/2000 | Rozell | 602/20 |

* cited by examiner

*Primary Examiner*—Denise Pothier
(74) *Attorney, Agent, or Firm*—Kevin Ellicott, Esq.

(57) ABSTRACT

A rehabilitative shoulder support comprising a supple sleeve component having a pair of elastically adjustable shoulder straps and a pair of downwardly depending elastic straps, a circumferential belt having a pair of shoulder strap circumferential belt loops, the circumferential belt loops being attached to elastically adjustable shoulder straps, the pair of downwardly depending elastic straps being permanently attached to the circumferential belt.

8 Claims, 4 Drawing Sheets

REHABILITATIVE SHOULDER SUPPORT

CROSS REFERENCE TO OTHER APPLICATIONS

This is the first submission of an application for this article of manufacture. There are no other applications, provisional or non provisional.

FEDERALLY SPONSORED RESEARCH AND DEVELOPMENT

There are no federally sponsored or funded research or development projects or undertakings in any way associated with the instant invention.

BACKGROUND OF THE INVENTION

1. Field of the Invention

The instant invention relates to that field of devices consisting of articles of manufacture known as shoulder supports. Specifically, the instant invention is a shoulder support for both supporting the shoulder joint and assisting in rehabilitation of damaged shoulder joints and the soft tissues surrounding them.

2. Background Information

It is well known in the prior art that the shoulder joint is a weak point in the human skeletal structure. On a daily basis, the shoulder joints will be called upon to act in a wide range of motions, including circumduction, abduction, flexion, extension, adduction and rotation. Unfortunately, a not infrequent occurrence is damage to component parts of the shoulder joint. One of the more common forms of damage is generally known as shoulder dislocation.

Dislocation of the shoulder is a truly painful experience, as anyone who has suffered from the same can testify. Following dislocation, there is usually, in addition to the actual damage to the joint, concomitant bruising and swelling of the surrounding tissue. The healing process may take weeks, months or longer. In some cases, those who have suffered these injuries remain permanently impaired, and subject to repeated dislocations while engaging in simple, physically non-demanding activities. In fact, some of those so injured believe that the injury never completely heals, and find themselves suffering repeated dislocations over time for no apparent reason. For these individuals, strenuous activity is not a prerequisite to shoulder dislocation. The simple act of using one's finger to scratch the back side of one's head may be enough to instigate a dislocation and set back recovery to nearly the point of the original injury.

During the period of recovery from such an injury, it has been a common practice to immobilize the injured area. Such immobilization has been accomplished in a variety of ways, including strapping the entire arm to the body, and rigidly supporting the arm and shoulder.

One serious drawback to such methods is that the complete immobilization of the injured area may lead to certain degrees of atrophy to the surrounding soft tissues. Furthermore, immobilization of the joint which entails immobilization of the entire arm (or at the very least the upper portion of the arm which includes the biceps muscle) is almost certain to result in a degree of atrophy to the arm's associated muscles.

Another serious drawback to complete immobilization of the shoulder joint is that the joint tends to "stiffen" with disuse. Many of those associated with the physical therapy profession have come to accept this drawback and direct much of their energies to assisting the injured person to regaining a full range of motion during rehabilitation following the physical recovery period. In fact, prolonged disuse of the shoulder may well contribute to the onset and or aggravation of arthritis in the joint.

Physical therapy during the recovery period often focuses on strengthening the muscles which surround the joint, supporting the joint and providing the motive forces required to move the joint through its range of motion. Unfortunately, the various forms of braces created to date may do more harm than good when it comes to strengthening shoulder muscles.

Prior art shoulder braces have generally focused on stabilization of the shoulder, and to that end have tended to utilize either rigid brace works or resilient strapping. A fine example of this latter form of brace may be found in U.S. Pat. No. 5,188,587, "Protective Shoulder Brace", issued on Feb. 23, 1993 to R. McGuire.

The McGuire '587 patent utilized a shoulder/arm cuff which had incorporated onto it four resilient straps, two of which would extend across the ventral and dorsal surfaces of the human body and cross over one another. Following the cross over, these two straps would be removably attached to a circumferential belt strap. The second set of straps would depend downwardly from the device, once again crossing over one another as did the first set of straps, and be removably attached to the circumferential belt strap.

This arrangement works in the manner claimed by its inventor. Unfortunately, Applicant has learned that efficacy of this sort of device declines rapidly once the shoulder injury begins to heal. In fact, Applicant believes that use of this sort of device may actually contribute to long-term shoulder joint difficulties. Because the stated object of the invention, to ensure that the shoulder joint does not dislocate, is accomplished by maintaining a constant force which pushes the components of the joint against one another, it is impossible to train the muscles supporting the joint to bear that weight without the support. In other words, by removing all stress and weight from the shoulder, the device has the unintended effect of weakening the very muscles which need strengthening in order for the joint to adequately heal.

A further disadvantage of the aforementioned device is that the utilization of resilient straps to limit motion (and potential dislocation) prevents the wearer from engaging in gradual self-rehabilitation. For example, Applicant is aware that the simple action of "shrugging" one's shoulders has a certain rehabilitative effect when done frequently over the course of a day. Such rehabilitative effect intensifies when a shoulder support is worn which provides limited resistance to the physical action of shrugging. Unfortunately, the device contemplated in McGuire '587 simply cannot accommodate such exercises. While it is possible for the wearer of the device to slacken the first set and/or second set of straps, such release of tension on the shoulder cuff simply makes the shrug possible while removing the support the device is intended to provide. The device cannot be used as a rehabilitative device in and of itself. It merely provides support to the shoulder in such a way as to permit the wearer to engage in other forms of rehabilitation while wearing it.

Applicant knows of only one other prior art invention which does not rely upon stiff or resilient strapping means to support a damaged shoulder. In U.S. Pat. No. 5,181,906, "Shoulder Joint Bandage", issued to H. Bauerfeind on Jan. 26, 1993, provision is made for an elastic material bandage which may be used to support the shoulder following dislocation injuries. In large part, the patent is directed to providing a bandage which would not cause irritation to the armpit of the wearer. The bandage comprised an elastic material cuff which was attached to a pair of straps. The pair of straps crossed the dorsal and ventral sides of the wearer's body and were stitched to a circumferential belt, the circumferential belt being capable of being cinched tight about the wearer's mid-body, proximate to the diaphragm.

Although it incorporated an elastic material which allowed the bandage to yield somewhat while being worn, the stated form of the bandage tended to allow the muscles of the shoulder joint to atrophy from disuse, and failed to provide any means for keeping the shoulder pulled downwardly. Thus, without any downward force being applied, the shoulder could be shrugged in such a way that not only could some exercise take place, but the entire shoulder could be once again dislocated with relative ease.

It is with these problems and others in mind that Applicant turns now to the solutions provided by her novel invention.

SUMMARY OF THE INVENTION

The instant invention is a rehabilitative shoulder support for maintaining the shoulder joint in a position most conducive to healing while at the same time providing adjustability for varying stages during the healing process and controlled limitations on movement for enabling ongoing daily self-rehabilitation.

A first object of the instant invention is to provide a shoulder support which is useful not only during the early stages of recovery from shoulder injuries when stabilization is important, but during the later stages when freedom of movement is required in order to adequately exercise the shoulder, yet still provide sufficient limitations on that movement so as to prevent re-injury to the shoulder.

Applicant accomplishes this objective by creating a rehabilitative shoulder support which includes a pliable sleeve component connected to a first set of adjustably elastic straps which are in turn removably and adjustably connected to a circumferential waist strap, the first set of adjustably elastic straps tending to keep the shoulder and arm portions of the shoulder joint in contact with one another. The instant invention further includes one or more downwardly depending elastic straps permanently attached to the circumferential waist strap which tend to keep the shoulder from being raised too far during the total period of recovery.

Another object of the instant invention is to provide a rehabilitative shoulder support which may be used as an exercise device during the course of the recovery period such that the wearer may engage in ongoing daily exercises and thus speed recovery and minimize the likelihood of atrophy to the surrounding muscles.

Applicant accomplishes this objective through the utilization of the first set of adjustably elastic straps which tend to bias the sleeve component toward the opposite shoulder and the one or more downwardly depending straps which tend to bias the portion of the shoulder cuff proximate to the wearer's armpit toward the wearer's waist. The biasing effect of the first and second set of straps requires that the wearer exert some force against the straps in order to move the shoulder through different positions, and thus permit the wearer of the device to use the opposing forces to engage in ongoing exercise of the injured shoulder throughout the day rather than only during discrete therapy sessions.

A further object of the instant invention is to provide a rehabilitative shoulder support which may be worn for extended periods (months to years) for both rehabilitative purposes and for limiting opportunities to re-injure the affected area.

Applicant accomplishes this objective by creating a rehabilitative shoulder support having adjustably elastic straps which tend to yield within user defined limits when pressure is applied to them such that the support may be worn comfortably on a daily basis, and still provide the support needed by the wearer to prevent accidental shoulder dislocation.

A further object of the instant invention is to provide a rehabilitative shoulder support which may be worn over extended periods (months to years) which may be cheaply and easily modified to provide both the differing amounts of support needed over time and the differing amounts of biasing force needed over time to continually strengthen the damaged shoulder.

Applicant achieves this objective by creating a rehabilitative should support having adjustably elastic straps which can be tightened or loosened so that the biasing force is varied. Elastically adjustable straps having differing biasing force may also be manufactured into the device.

A further object of the instant invention is to provide a rehabilitative shoulder support which may be quickly and efficiently converted to act as a sling, thereby offering still more shoulder support.

Applicant accomplishes this objective by including an additional support strap which functions not simply to provide support to the circumferential waist belt, but also to function as a sling by being attached to a third, short strap which connects directly to the additional support strap.

A further object of the instant invention is to provide a rehabilitative shoulder support capable of providing an adduction exercise function.

Applicant accomplishes this objective by including an elastic adduction strap which may be attached to the sleeve component and the circumferential belt, the elastic adduction strap providing a downward biasing force against which the wearer of the instant invention may exert force while lifting the arm and thus help strengthen the injured shoulder.

Finally, Applicant believes that the instant invention may be utilized in conjunction with a cold pack or hot pack to alleviate pain and speed recovery. This object is accomplished by utilizing a sleeve component under which may be placed a cold or warm pack or compress so that it is in direct contact with the injured area and held in place there by the sleeve component.

A DESCRIPTION OF THE PREFERRED EMBODIMENT

Figure 1:
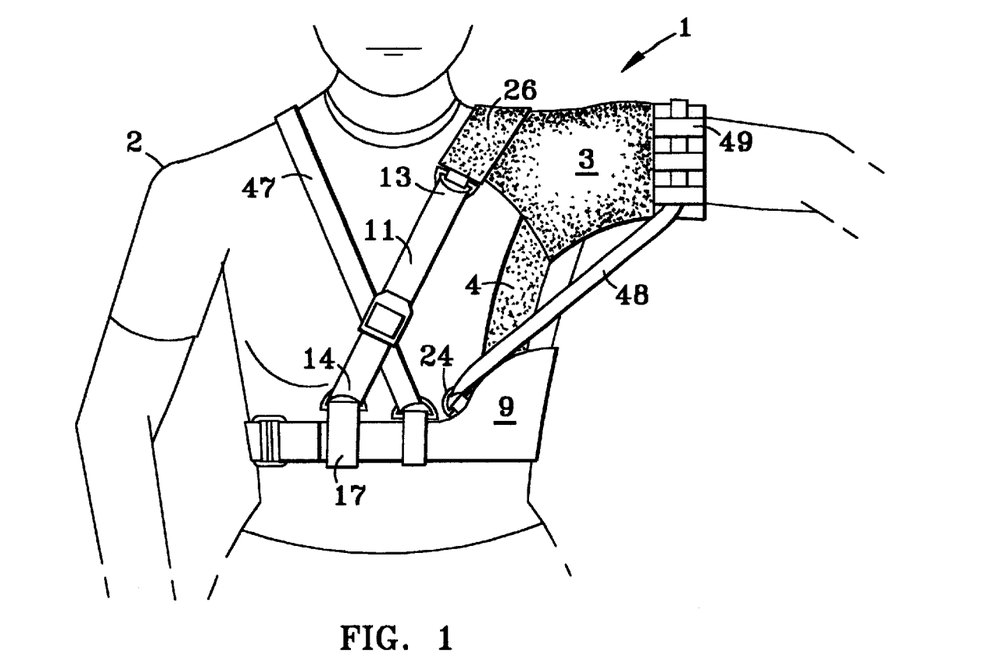
FIG. 1 is a perspective view of the instant invention in place on a wearer.

As per FIG. 1, the instant invention is a rehabilitative shoulder support (1) shown in place on a wearer (2). For understanding's sake, the wearer is assumed to have an injured left shoulder, and the wearer's arm is outstretched and elevated.

Figure 2:
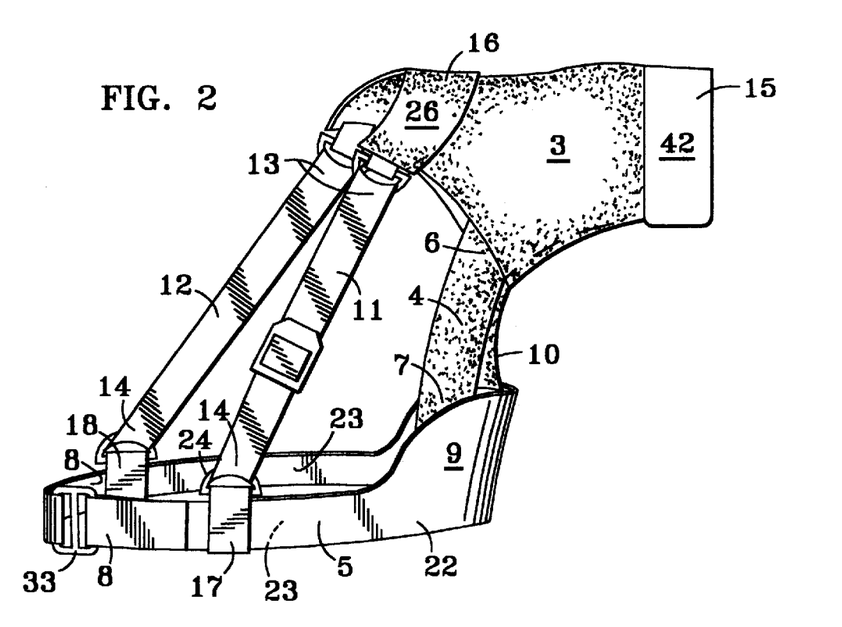
FIG. 2 is another perspective view of the instant invention.

As per FIGS. 1 and 2, the instant invention has a sleeve component (3). The sleeve component is constructed such that it conforms to the shape of the wearer's shoulder and completely encircles the wearer's upper arm. Applicant believes that the sleeve component should be composed of a material which is somewhat supple and elastic. In the preferred embodiment, Applicant constructs the sleeve component from Neoprene; however, other materials which have a relatively smooth texture, which will conform to the wearer's shoulder and arm, and which are somewhat elastic would work equally well. It should be remembered that the rehabilitative shoulder support could potentially be worn up to 24 hours each day, and for extended periods of time (weeks to months, months to years). Therefore, it is extremely important that the material from which the sleeve component is made not be rough to the touch, and be supple so that extended wear does not produce discomfort or injuries to the skin underlying the sleeve component.

The sleeve component (3) may be further described as having a sleeve component arm portion (15) and an opposite sleeve component shoulder portion (16). The sleeve component arm portion (15) will be circumferentially in direct contact with the wearer's arm, in approximately the biceps muscle region of the arm, when the instant invention is being worn. The sleeve component shoulder portion (16) will overlie the distal end of the wearer's clavicle, acromion, greater tubercle and proximal end of the humerus when the instant invention is being worn.

The sleeve component utilizes a number of elastic straps in its construction, and the locations of these elastic straps in the completed device will now be more clearly detailed. As per FIGS. 2 and 4, the sleeve component incorporates first elastic strap (26) which is permanently attached to the sleeve component. The first elastic strap (26) is located on the sleeve component at the end of the sleeve component most proximate to the wearer's neck when the device is being worn, along the sleeve component shoulder portion (16). The first elastic strap (26) has a first elastic strap first end (27) and an opposite first elastic strap second end (28). Applicant permanently attaches to the first elastic strap first end (27) a "D" ring (24). Applicant also permanently attaches to the first elastic strap second end (28) a "D" ring (24). This permanent attachment may be accomplished in many ways, but Applicant prefers to utilize a resilient strap having a first end and a second end which is wrapped through the opening in the "D" ring and back around on itself so that the "D" ring is held by the resilient strap, and then sewing the first end and the second end to the first elastic strap, thereby permanently securing the "D" ring to the first elastic strap. Applicant believes that the so-called "D" ring is optimal for attaching various straps to various portions of the instant invention. The "D" ring together with the resilient strap is simply the strap attachment means preferred by Applicant. However, while Applicant prefers to utilize as the strap attachment means a "D" ring with its attached resilient strap, other strap attachment means would work equally well so long as they permit the strap to pivot somewhat relative to the portion of the instant invention to which the strap is to be attached. This ability to pivot provides a greater range of motion while the device is being worn, and further tends to decrease the possibility of being "pinched" by the various straps while moving one's body during exercise.

Figure 5:
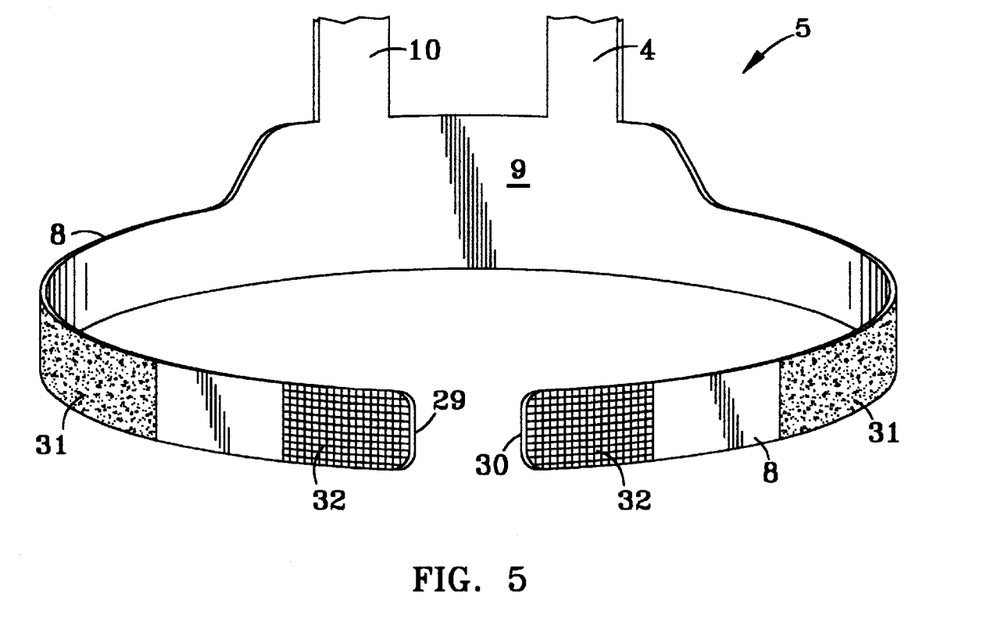
FIG. 5 is a perspective view of the circumferential belt.

As per FIGS. 1, 2 and 5, the sleeve component (3) has depending downwardly therefrom a first circumferential belt connector (4) and a second circumferential belt connector (10) which are both directly attached to a circumferential belt (5). In the preferred embodiment, the circumferential belt is essentially a strip of elastic material sufficiently long to extend around and encompass the torso of the wearer, positioned such that it will not restrict the breathing of the wearer, the circumferential belt having a first end (29) and an opposite second end (30).

The first circumferential belt connector (4) and the second circumferential belt connector (10) are each a strap of elastic material having a circumferential belt connector first end (6) and an opposite circumferential belt connector second end (7), the circumferential belt connector first end (6) being permanently attached to the sleeve component (3), the circumferential belt connector second end (7) being permanently attached to the circumferential belt (5). The first circumferential belt connector (4) and the second circumferential belt connector (10) may be further understood to be attached to the sleeve component (3), the area of attachment being approximately midway between the sleeve component arm portion (15) and the sleeve component shoulder portion (16), such that when the device is worn, the first circumferential belt connector and the second circumferential belt connector rest against the torso of the wearer, near the arm pit of the wearer. When the device is being worn, the first circumferential belt connector will be in contact with the wearer's torso, approximately overlying the serratus anterior muscle while the second circumferential belt connector will be in contact with the wearer's torso, approximately overlying the latissimus dorsi, the first circumferential belt connector and second circumferential belt connector being parallel to, though not coplanar with, one another. In the preferred embodiment, the first circumferential belt connector and second circumferential belt connector are both non-adjustable and are permanently attached to the circumferential belt and the sleeve component by suitable means such as sewing, chemical attachment (such as glue) or other suitable means. The first circumferential belt connector and the second circumferential belt connector should be constructed from an elastic material having sufficient elasticity to bias the sleeve component downwardly, toward the circumferential belt.

Applicant has learned that by utilizing different materials having different elasticity when constructing the circumferential belt connectors, it is possible to provide differing amounts of downward biasing force, and thus change the amount of tension on the sleeve component. This makes it possible to fabricate the device such that it provides greater or lesser amounts of force to be applied upwardly by the wearer in order to shrug the shoulder when the device is being worn. This, in turn, allows for a rehabilitative device which may be used to exercise the shoulder rather than simply restraining it. In other words, one may use a more elastic material (one providing less biasing force) when fabricating the circumferential belt connectors to be used on the instant invention when it is to be worn by a person having a recent injury, and then use a less elastic material later to fabricate the circumferential belt connectors when the wearer's injury has undergone healing, and further rehabilitation of the shoulder requires that more biasing force present when the wearer attempts a shoulder shrug. However, in any case the first circumferential belt connector and the second circumferential belt connector must be made of an elastic material in order for the device to function properly.

As per FIGS. 1, 2 and 5, the circumferential belt (5) may be further described as having a narrow section (8) and a wide section (9). In the preferred embodiment of the instant invention, the first circumferential belt connector second end and the second circumferential belt connector second end are both attached to the circumferential belt wide section (9). Applicant has found that inclusion of the wide section (9) directly below the arm pit of the wearer of the article results in a more stable device which is less likely to twist or double over on itself when the wearer is engaged in physical activity. The circumferential belt (5) further has a circumferential belt outer surface (22) and an opposite circumferential belt inner surface (23). The circumferential belt inner surface will be understood to be that surface of the circumferential belt which is in direct contact with the body of the wearer when the instant invention is being worn.

Applicant prefers to construct the circumferential belt so that the outer surface (22) along the circumferential belt narrow section (8), has thereupon the loop portion (31) of a so-called hook and loop material (also known as "VELCRO"). The loop portion of the material is permanently attached, preferably by sewing, to the circumferential belt. Proximate to the circumferential belt first end (29), Applicant permanently attaches a hook portion (32) of the hook and loop material. Proximate to the circumferential belt second end (30), also on the outer surface (22), Applicant permanently attaches a hook portion (32) of the hook and loop material. The hook portion (32) need only be large enough to securely, but removably, attach the hook portion to the loop portion.

Figure 6:
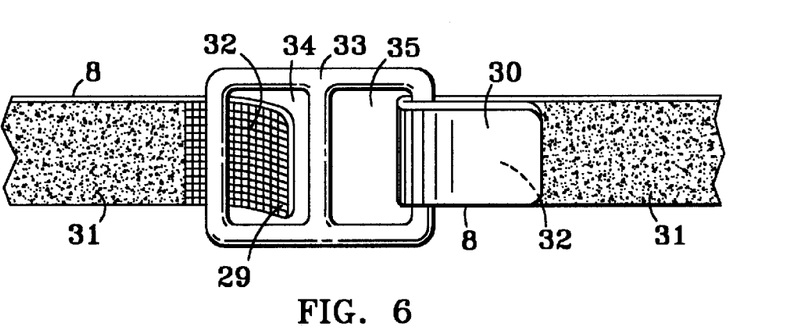
FIG. 6 is a perspective view of the circumferential belt and buckle.

When worn by the user, as per FIGS. 1, 5 and 6, the circumferential belt first end (29) is placed through the first opening (34) of a buckle (33) and wrapped back onto itself such that the hook portion (32) proximate to the first end (29) comes into contact with the loop portion along the circumferential belt narrow section (8). So too, the circumferential belt second end (30) is placed through the second opening (35) of the buckle and wrapped back (or folded over) onto itself so that the hook portion (32) proximate to the second end (30) comes into contact with the loop portion (31) along the circumferential belt narrow section. In this manner, the circumferential belt may be easily adjusted to fit various torso circumferences. Should the circumferential belt be worn by someone very thin (having a smaller torso circumference) the circumferential belt first end (29) would be pulled through the buckle so that the first end (29) would be more proximate to the circumferential belt wide section (9) when the hook portion (32) on the first end (29) was placed into contact with the loop portion (31) on the circumferential belt narrow section (8). Obviously, the circumferential belt second end (30) would be adjusted in the same manner. Also, the buckle referred to above may be most simply understood as a body (preferably square in form) having two openings passing through it. In this simple buckle (33), one hole (the first opening) is utilized for passing the circumferential belt first end through, and the second hole (the second opening) is utilized for passing the circumferential belt second end through.

The instant invention further has a first shoulder strap (11) and a second shoulder strap (12). The first shoulder strap (11) and the second shoulder strap (12) each have a shoulder strap first end (13) and a shoulder strap second end (14). In the preferred embodiment, both the first shoulder strap first end and the second shoulder strap first end are attached to sleeve component (3). This is accomplished by permanently attaching the first shoulder strap (11) first end (13) to the "D" ring located on the first elastic strap first end (27), and permanently attaching the second shoulder strap (12) first end (13) to the "D" ring located on the first elastic strap second end (28).

Applicant prefers to attach the first shoulder strap first end (13) to the first elastic strap first end "D" ring by wrapping the first shoulder strap through the "D" ring and folding the first shoulder strap first end back onto itself. The first shoulder strap first end is then sewn onto the first shoulder strap so that it is permanently attached to the first elastic strap first end "D" ring. The second shoulder strap first end is attached to the first elastic strap second end (28) "D" ring in the same manner.

Figure 3:
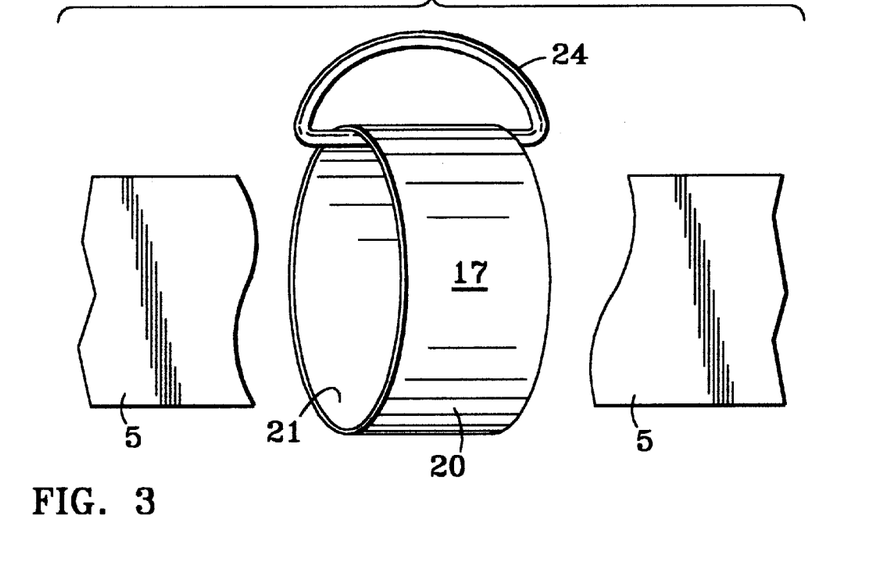
FIG. 3 is a close up perspective view of a shoulder strap circumferential belt loop having a "D" ring.

As per FIGS. 2 and 3, in the preferred embodiment, the first shoulder strap and the second shoulder strap are each adjustably attached to the circumferential belt (5). Applicant accomplishes the adjustable attachment by utilizing a first shoulder strap to circumferential belt loop (17) having a "D" ring, and a second shoulder strap to circumferential belt loop (18) having a "D" ring. The first shoulder strap circumferential belt loop (17) is a strap having a first end and a second end, a strap outer surface (20) and a strap inner surface (21), the strap being wrapped around the circumferential belt (5), through the "D" ring, and the strap first end being permanently connected to the strap second end, thus forming a loop with an attached "D" ring. The second shoulder strap circumferential belt loop (18) having a "D" ring is identical to the first shoulder strap circumferential belt loop (17) having a "D" ring. Both the first and second shoulder strap circumferential belt loops should be of sufficient dimensions to permit them to be moved along the circumferential belt narrow section (8), but not so large as to allow them to move along the circumferential belt wide section (9), once attached to the circumferential belt (5). When assembled in this fashion, the strap inner surface may come into direct contact with the circumferential belt.

Applicant prefers to construct the first and second shoulder strap circumferential belt loops from a resilient material such as nylon. Applicant has found that so-called "ballistic nylon" works especially well for this purpose. Furthermore, Applicant utilizes the two piece hook and loop material, also known as "VELCRO" when constructing the first and second shoulder strap circumferential belt loops. The hook portion of the material is permanently attached, preferably by sewing, to the first shoulder strap circumferential belt loop strap inner surface (21). Again, as was noted above, the first shoulder strap circumferential belt loop strap (17) and the second shoulder strap circumferential belt loop strap (18) are identical.

As the first shoulder strap circumferential belt loop strap (17) and the second shoulder strap circumferential belt loop strap (18) each have on their inner surface the hook portion of the hook and loop material, the first shoulder strap circumferential belt loop strap (17) and the second shoulder strap circumferential belt loop strap (18) may be securely but removably attached in place to the circumferential belt (5). That is, once moved into position along the circumferential belt, the wearer merely presses firmly against the first shoulder strap circumferential belt loop strap and the second shoulder strap circumferential belt loop strap to secure them in place along the circumferential belt. The purpose of such securing will be more fully described below.

Figure 7:
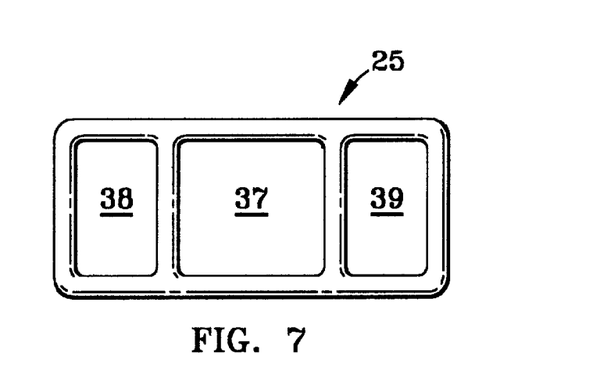
FIG. 7 is a plan view of the strap adjuster.

In addition to the first shoulder strap and second shoulder strap being adjustably attached to the circumferential belt, the first shoulder strap and the second shoulder strap are adjustable. In the preferred embodiment this is accomplished by threading the first shoulder strap through an adjustable buckle (25) prior to wearing the instant invention. As per FIG. 7, Applicant prefers to use an adjustable buckle of the sort commonly known as a strap adjuster (25). A strap adjuster is similar to the buckle (33) described earlier, however instead of having two openings, the type preferred by Applicant has three openings. Those skilled in the art will be well aware that to utilize a strap adjuster, one threads a free end of a strap up through a strap adjuster first opening (37), down through a strap adjuster second opening (38), folding the strap back over onto itself (thus producing a loop) and back up through the second opening (38), and down through a third opening (39).

Finally, the "elastic adjustability" of the shoulder straps may now be better understood. As per FIGS. 1, 2 and 4, the first shoulder strap (11) and the second shoulder strap (12) are each connected to the first elastic strap (26) via "D" rings. The opposite ends of the first shoulder strap (11) and the second shoulder strap (12) are each connected, respectively, to the circumferential belt (5) via the first shoulder strap to circumferential belt loop (17) having a "D" ring and second shoulder strap to circumferential belt loop (18) having a "D" ring. Furthermore the first shoulder strap (11) and the second shoulder strap (12) each can have a strap adjuster (25).

When the wearer of the device wishes to increase the amount of tension (or forces pulling the shoulder portion toward the neck of the wearer and toward the portion of the circumferential belt directly opposite the circumferential belt wide section) on the sleeve component, all that is required is that the first shoulder strap and second shoulder strap be "shortened" by utilizing the strap adjusters. That is, by pulling the first shoulder strap and the second shoulder strap and moving the strap adjuster to take up any slack in the first shoulder strap and second shoulder strap, the sleeve component is pulled tighter against the shoulder. However, because the first shoulder strap and second shoulder strap are each attached to the first elastic strap (26) both the first shoulder strap and the second shoulder strap will act not simply as a resilient strap, thus immobilizing the shoulder, but rather will tend to bias the sleeve component shoulder portion toward the neck and the circumferential belt, as explained above.

In other words, the wearer of the instant invention has a wide range of options available in terms of the amount of force being applied to hold the shoulder in place. When wearing the device immediately following an injury to the shoulder, the first shoulder strap and second shoulder strap may be adjusted so that they exert a larger amount of biasing force against the shoulder, and thus limit motion of the shoulder without immobilizing it (because the first elastic strap provides some "give" or elasticity to the first shoulder strap and second shoulder strap). However, as time passes and the injury begins to heal, the first shoulder strap and second shoulder strap may be loosened somewhat. While the biasing effect of the first elastic strap will still be present, the amount of force needed to overcome the biasing force will be decreased, thus allowing the wearer more freedom of movement while still providing the injured shoulder with support.

Applicant believes the first shoulder strap and second shoulder strap are elastically adjustable in another manner. As was noted above, the first shoulder strap to circumferential belt loop (17) having a "D" ring and second shoulder strap to circumferential belt loop (18) having a "D" ring each have so-called "hook" material on their inner surface. Also, the circumferential belt has so-called "loop" material on its outer surface. Furthermore, both the first shoulder strap to circumferential belt loop (17) and the second shoulder strap to circumferential belt loop (18) are sized such that they may be slid along the circumferential belt narrow section (8). Applicant believes that sliding the first shoulder strap to circumferential belt loop (17) and second shoulder strap to circumferential belt loop (18) along the circumferential belt, either toward the wide section (9) or away from it tends to change the angle of the first shoulder strap (II) and the second shoulder strap (12) relative to the circumferential belt (5). It is Applicant's belief that this change of angle tends to somewhat modify the directions of force (biasing) being applied to the sleeve component, and thus to the shoulder of the wearer when the device is being worn. For example, when the first shoulder strap and second shoulder strap are moved along the circumferential belt, away from the circumferential belt wide section (9), the sleeve component tends to be pulled more toward the neck of the wearer when the device is being worn, thus "lifting" the shoulder more in the direction of the neck of the wearer. However, when the first shoulder strap and second shoulder strap are moved along the circumferential belt more towards the wide section, the biasing of the sleeve component shoulder portion is more downward, toward the circumferential belt.

Applicant believes that adjustment of the angle of the first shoulder strap and second shoulder strap relative to the circumferential belt provides the wearer of the device with still more options in terms of rehabilitative exercises. The combination of the adjustment of the angle of the first shoulder strap and second shoulder strap relative to the circumferential belt and the variable biasing force provided by the first elastic strap (26) allows the wearer of the instant invention to quickly and easily modify the configuration of the instant invention to perform different exercises requiring different amounts of resistive force in different directions. By way of examples, when the first shoulder strap and second shoulder strap have been positioned such that the first shoulder strap to circumferential belt loop (17) and second shoulder strap to circumferential belt loop (18) are located distally from the circumferential belt wide section, less force is required in order to "shrug" the shoulder upon which the device is worn. However, in that same position, more force is required in order for the wearer of the device to push both shoulders back (thus "squaring" the shoulders). Conversely, when the first shoulder strap and the second shoulder strap have been positioned such that the first shoulder strap to circumferential belt loop and second shoulder strap to circumferential belt loop are proximate to the circumferential belt wide section, less force would be required to "square" the shoulders while more force would be required to "shrug". Furthermore, it should be remembered that the overall length of the first shoulder strap and second shoulder strap is adjustable via the strap adjusters, and therefore the biasing force against the shoulder (due to the first elastic strap being pulled against by the first shoulder strap and second shoulder strap, when so adjusted) may be changed in concert with the change of angle relative to the circumferential belt. Thus, another level of elastic adjustablility of the first shoulder strap and second shoulder strap is achieved.

Figure 4:
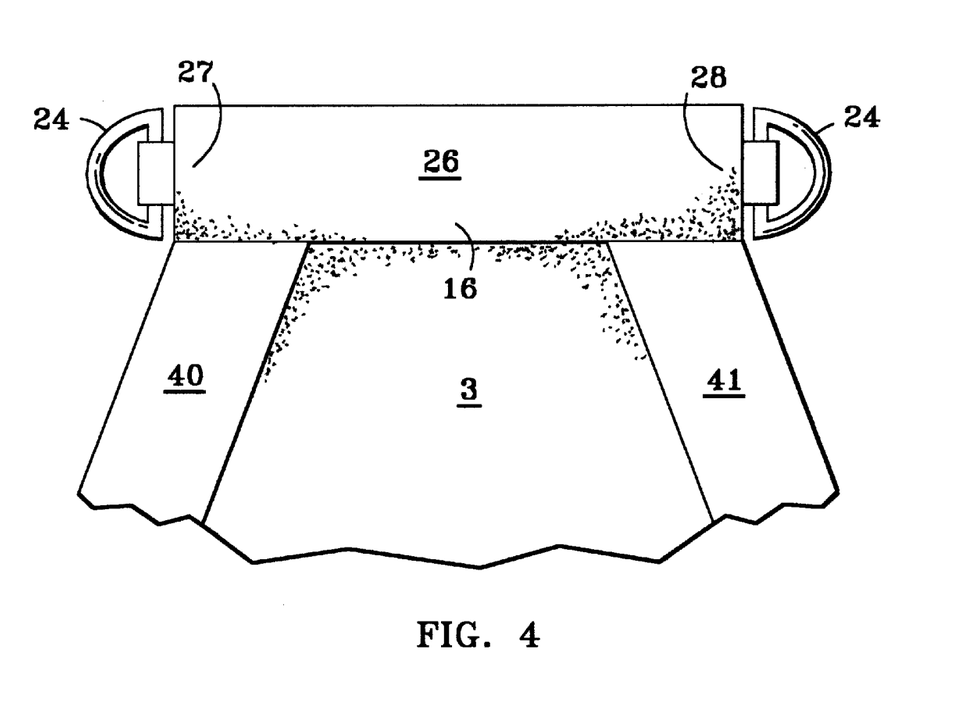
FIG. 4 is an overhead plan view of a portion of the sleeve component.
Figure 8:
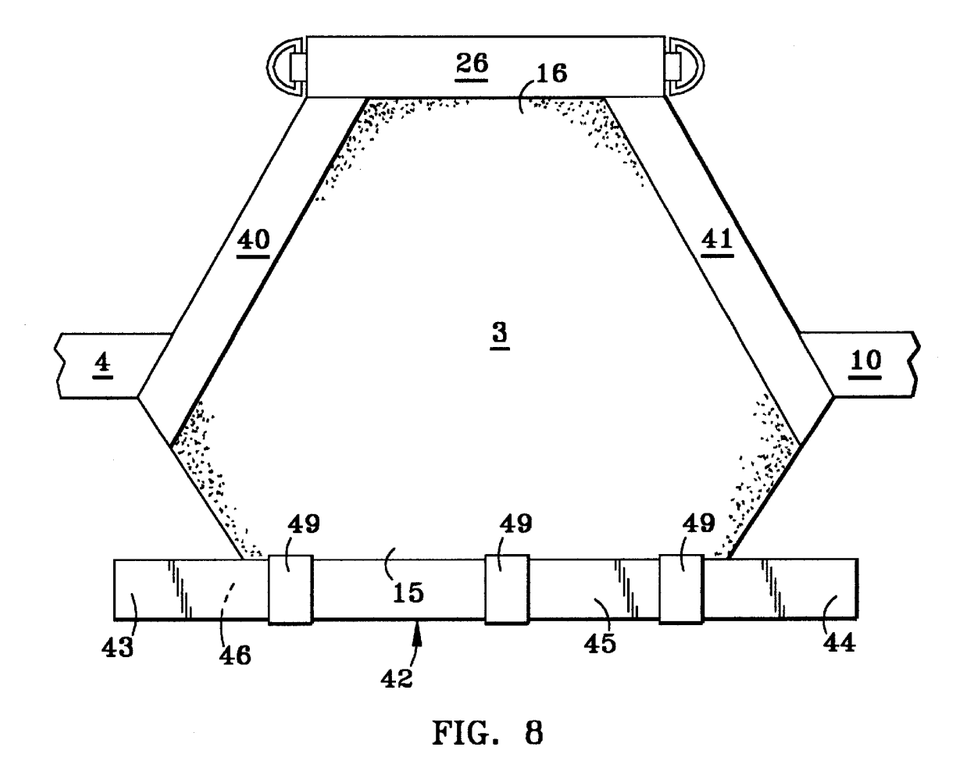
FIG. 8 is a plan view of the disassembled sleeve component.

As per FIGS. 4 and 8, Applicant further believes that it may be useful to include a second elastic strap (40), a third elastic strap (41) and a fourth elastic strap (42). The second elastic strap, third elastic strap and fourth elastic strap are all permanently attached to the sleeve component (3).

The precise arrangement of the second, third and fourth elastic straps will be better understood following a discussion of the shape of the sleeve component (3). As per FIG. 8, prior to assembly into the completed device, the sleeve component is essentially a flattened piece of material having the form of a hexagon. The first elastic strap has previously been described as being attached to the shoulder portion of the sleeve component. It will be further understood as being attached along one side of the hexagonally shaped sleeve component. The second elastic strap (40) and the third elastic strap (41) are permanently attached to the sleeve component, adjacent to and intersecting the first elastic strap. Applicant prefers that the second elastic strap intersects the first elastic strap at the first end of the first elastic strap. Applicant prefers that the third elastic strap intersects the first elastic strap at the second end of the first elastic strap.

The fourth elastic strap (42) is attached to the sleeve component (3) at the sleeve component arm portion (15), directly opposite the first elastic strap (26). The fourth elastic strap has a first end (43) and an opposite second end (44). The fourth elastic strap further has a outer surface (45) and an inner surface (46), the inner surface being that surface which is in direct contact with the arm of the wearer of the device when the device is completely assembled and worn. The fourth elastic strap should be of sufficient length to completely wrap circumferentially around the upper arm of the wearer. Applicant prefers to permanently attach loop material of the sort described earlier, to the inner surface (46) of the fourth elastic strap, proximate to the fourth elastic strap first end (43). Applicant further prefers to permanently attach hook material of the sort described earlier to the outer surface (45) of the fourth elastic strap, proximate to the second end (44) of the fourth elastic strap.

When assembled into the completed device, the sleeve component (3) encompasses the shoulder of the wearer, but leaves the area of the wearer's arm pit uncovered. Applicant has found that this makes the device far more comfortable to wear for extended periods.

Furthermore, when completely assembled and worn, the fourth elastic strap (42) is wrapped around the wearer's arm, completely encircling the arm. By tightening the fourth elastic strap around the upper arm, the wearer of the device ensures that the sleeve component will not tend to "creep" or gradually move along the surface of the shoulder toward the neck of the wearer. This tendency to creep is further diminished by the force of the first circumferential belt connector (4) and the second circumferential belt connector (10) pulling downwardly on the sleeve component.

Applicant has found that by also attaching the first elastic strap (through sewing or similar means) to both the second elastic strap and the third elastic strap as well as attaching the first circumferential belt connector to the second elastic strap and the second circumferential belt connector to the third elastic strap (both connections being made by sewing or similar means), the second elastic strap (40) and the third elastic strap (41) both tend to more evenly distribute the biasing forces of the first shoulder strap and second shoulder strap, as well as the first circumferential belt connector and the second circumferential belt connector by allowing the sleeve component to "give" or yield somewhat more than would a sleeve component not having such second and third elastic straps. Applicant believes that this further increases the "elastic adjustability" of the first and second shoulder straps.

In another embodiment of the instant invention, Applicant includes a support strap (47) and a "sling" strap (not shown). As per FIG. 1, the support strap is a single strap constructed from resilient material (such as nylon or ballistic nylon) having a first end and a second end, a inner surface and outer surface and of sufficient length such that the first end may be attached to the circumferential belt, proximate to the wide section, and then be placed in direct contact with the ventral surface of the wearer's torso (the support strap inner surface being in contact with the wearer's torso), reach upwardly and over the shoulder (the shoulder opposite of the injured shoulder), and continue down the ventral surface of the wearer's torso, in direct contact with that dorsal surface, the second end connecting to the circumferential belt, again proximate to the circumferential belt wide section. Applicant prefers that the support strap include a strap adjuster so that it may be worn comfortably by simply adjusting the length of the support strap. The support strap is attached to the circumferential belt in the same manner as is the first shoulder strap (11), however it is positioned along the circumferential belt in the manner set forth immediately above. Furthermore, when used to attach the support strap to the circumferential belt, one may instead call the first circumferential belt loop having a D-ring a first support strap belt loop having a D-ring. So too, the second circumferential belt loop having a D-ring may instead be called a second support strap belt loop having a "D" ring.

The sling strap is a single strap made from either resilient or elastic material. The sling strap has a first end and a second end, a top surface and a bottom surface. Applicant permanently attaches hook material to the top surface, proximate to the first end. Applicant permanently attaches loop material to the bottom surface, proximate to the second end. Once the instant invention is being worn by the wearer, the sling strap is wrapped under the support strap (47) such that the sling strap top surface is in contact with the support strap and the sling strap bottom surface is in contact with the wearer. The arm attached to the injured shoulder is then placed with the wrist against the support strap outer surface, in direct contact with and overlying the sling strap. The sling strap is then wrapped over the wrist and the hook material pressed against the loop material thus securing the arm to the support strap, and providing a sling which may be worn over clothing or in direct contact with the wearer's body, under clothing (just as the rehabilitative shoulder support may be worn).

In another embodiment of the instant invention, as per FIGS. 1 and 8, Applicant incorporates an elastic adduction exercise strap (48). The elastic adduction exercise strap may be useful in order to further rehabilitate the shoulder by providing resistance when the user of the instant invention attempts to lift the arm attached to the injured shoulder, for instance, when attempting to touch the top of the wearer's head.

The elastic adduction strap may be easily constructed from the same material as are the first circumferential belt connector (4) and the second circumferential belt connector (10). The elastic adduction strap has a first end and a second end, the first end being attached to strap retainer means (24) permanently attached to the circumferential belt, proximate to the circumferential belt wide section (the circumferential belt wide section located in contact with the wearer's ventral surface). The second end is attached to strap retainer means (24) permanently attached to the circumferential belt, proximate to the circumferential belt wide section (the circumferential belt wide section located in contact with the wearer's dorsal surface).

Proper functioning of the elastic adduction strap requires that a plurality of adduction strap to fourth elastic strap (42) retainers (49) be included. In the preferred embodiment, these retainers (49) are resilient straps which are permanently attached to the fourth elastic strap, each retainer having a first end and a second end. Only the first end and the second end of each retainer are permanently attached to the fourth elastic strap such that the elastic adduction strap (48) may be passed underneath each retainer strap, between the retainer strap and the fourth elastic strap, thereby securing the elastic adduction strap to the fourth elastic strap. Obviously, where any strap has a first end and a second end, it also has a middle section. In the case of the retainer, the middle is not attached to the fourth elastic strap. Furthermore, the retainers are attached to the fourth elastic strap such that they are perpendicular to the fourth elastic strap (the fourth elastic strap being longer than it is wide, the retainer being perpendicular to the fourth elastic strap length).

The elastic adduction strap (48) may be permanently attached to the "D" rings, however, Applicant believes it is better to include hook and loop material on the adduction strap and configure the strap to attach to the "D" rings in the same manner as the circumferential belt attaches to the buckle (33) as described above and in FIG. 6. Applicant also believes it may be desirable to utilize a strap adjuster with the elastic adduction strap so that the user of the instant invention can vary the force required in order lift the arm attached to the injured shoulder, thereby modifying the rehabilitative effect of the elastic adduction strap. The elastic adduction strap is extremely useful over time to the wearer of the device as it allows the wearer to increase or decrease the biasing force which tends to keep the arm pulled downwardly, toward the body. This represents a considerable break with the prior art as it provides the wearer with a means for exercising the injured shoulder at any time while the device is being worn by allowing the wearer to utilize the arm and shoulder to overcome the downward biasing force of the elastic adduction strap and thereby strengthen the injured shoulder instead of merely strapping the shoulder and arm into a fixed position.

I claim:

1. A rehabilitative shoulder support comprising;
   A. a sleeve component,
      I. the sleeve component having an arm portion and a shoulder portion,
   B. a first elastic strap,
      I. the first elastic strap being attached to the sleeve component shoulder portion,
   C. a first elastically adjustable shoulder strap,
      I. the first elastically adjustable shoulder strap having a first end and a second end,
         a. the first elastically adjustable shoulder strap first end being attached a the first elastic strap first end by strap attachment means,
   D. a second elastically adjustable shoulder strap,
      I. the second elastically adjustable shoulder strap having a first end and a second end,
         a. the second elastically adjustable shoulder strap first end being attached to a first elastic strap second end by strap attachment means,
   E. a first circumferential belt connector,
      I. the first circumferential belt connector having a first end and a second end,
         a. the first circumferential belt connector first end being attached to the sleeve component, midway between the arm portion and the shoulder portion,
   F. a second circumferential belt connector,
      I. the second circumferential belt connector having a first end and a second end,
         a. the second circumferential belt connector first end being attached to the sleeve component, midway between the arm portion and the shoulder portion,
   G. a circumferential belt,
      I. the circumferential belt having a first end and a second end,
      II. the circumferential belt having a wide section and a narrow section,
      III. the circumferential belt having an inner surface and an outer surface,
         a. the circumferential belt having hook and loop material located on the circumferential belt narrow section outer surface, proximate to the circumferential belt first end,
         b. the circumferential belt having hook and loop material located on the circumferential belt narrow section outer surface, proximate to the circumferential belt second end,
      IV. the circumferential belt wide section having attached thereto the first circumferential belt connector second end,
      V. the circumferential belt wide section having attached thereto the second circumferential belt connector second end,
   H. a buckle,
      I. the buckle having a first opening for passage therethrough of the circumferential belt first end,
      II. the buckle having a second opening for passage therethrough of the circumferential belt second end,
   I. a first circumferential belt loop having a D-ring,
      I. the first circumferential belt loop having a D-ring being slidably attached to the circumferential belt, proximate to the circumferential belt second end,
      II. the first circumferential belt loop having a D-ring being attached to the first elastically adjustable shoulder strap second end,
   J. a second circumferential belt loop having a D-ring,
      I. the second circumferential belt loop having a D-ring being slidably attached to the circumferential belt, proximate to the circumferential belt first end,
      II. the second circumferential belt loop having a D-ring being attached to the second elastically adjustable shoulder strap second end.

2. The rehabilitative shoulder support according to claim 1, the sleeve component being hexagonal in form.

3. The rehabilitative shoulder support according to claim 2, the sleeve component further comprising;
   A. a second elastic strap,
      I. the second elastic strap having a first end and a second end,
         a. the second elastic strap being permanently attached to the periphery of the sleeve component such that the second elastic strap first end and the first elastic strap first end are adjacent to one another,
   B. a third elastic strap,
      I. the third elastic strap having a first end and a second end,
         a. the third elastic strap being permanently attached to the periphery of the sleeve component such that the third elastic strap first end and the first elastic strap second end are adjacent to one another,
   C. a fourth elastic strap,
      I. the fourth elastic strap having a first end and a second end,
         a. the fourth elastic strap being permanently attached to the sleeve component, along the periphery of the sleeve component arm portion, parallel to the first elastic strap.

4. The rehabilitative shoulder support according to claim 1 further comprising:

A. a plurality of retainers
   I. the retainers each having a first end and a second end,
      a. the first end and second end being attached to the fourth elastic strap
B. an elastic adduction exercise strap,
   I. the elastic adduction exercise strap having a first end and a second end,
   II. the elastic adduction strap passing between the retainers and the fourth elastic strap,
   III. the elastic adduction exercise strap first end being attached to strap attachment means
      a. the strap attachment means being permanently attached to the circumferential belt, proximate to the circumferential belt wide section,
   IV. the elastic adduction exercise strap second end being attached to strap attachment means,
      a. the strap attachment means being permanently attached to the circumferential belt, proximate to the circumferential belt wide section.

5. The rehabilitative shoulder support according to claim 1 further comprising;
A. a support strap,
   I. the support strap having a first end and a second end,
B. a first support strap end-to-circumferential belt loop having a D-ring,
   I. the support strap first end being attached to the first support strap belt loop having a D-ring,
C. a second support strap belt loop having a D-ring,
   I. the support strap second end being attached to the second support strap belt loop having a D-ring.

6. A rehabilitative shoulder support comprising;
A. a sleeve component,
   I. the sleeve component having an arm portion and a shoulder portion,
   II. the sleeve component being hexagonal in shape,
B. a first elastic strap,
   I. the first elastic strap being attached to the sleeve component shoulder portion,
C. a second elastic strap,
   I. the second elastic strap having a first end and a second end,
      a. the second elastic strap being permanently attached to the periphery of the sleeve component such that the second elastic strap first end and the first elastic strap first end are adjacent to one another,
D. a third elastic strap,
   I. the third elastic strap having a first end and a second end,
      a. the third elastic strap being permanently attached to the periphery of the sleeve component such that the third elastic strap first end and the first elastic strap second end are adjacent to one another,
E. a fourth elastic strap,
   I. the second elastic strap having a first end and a second end,
      a. the fourth elastic strap being permanently attached to the sleeve component, along the periphery of the sleeve component arm portion, parallel to the first elastic strap.
F. a first elastically adjustable shoulder strap,
   I. the first elastically adjustable shoulder strap having a first end and a second end,
      a. the first elastically adjustable shoulder strap first end being attached to a first elastic strap first end by strap attachment means,
G. a second elastically adjustable shoulder strap,
   I. the second elastically adjustable shoulder strap having a first end and a second end,
      a. the second elastically adjustable shoulder strap first end being attached to a first elastic strap second end by strap attachment means,
H. a first circumferential belt connector,
   I. the first circumferential belt connector having a first end and a second end,
      a. the first circumferential belt connector first end being attached to the second elastic strap second end,
F. a second circumferential belt connector,
   I. the second circumferential belt connector having a first end and a second end,
      a. the second circumferential belt connector first end being attached to the third elastic strap second end,
G. a circumferential belt,
   I. the circumferential belt having a first end and a second end,
   II. the circumferential belt having a wide section and a narrow section,
   III. the circumferential belt having an inner surface and an outer surface,
      a. the circumferential belt having hook and loop material located on the circumferential belt narrow section outer surface, proximate to the circumferential belt first end,
      b. the circumferential belt having hook and loop material located on the circumferential belt narrow section outer surface, proximate to the circumferential belt second end,
   IV. the circumferential belt wide section having attached thereto the first circumferential belt connector second end,
   V. the circumferential belt wide section having attached thereto the second circumferential belt connector second end,
H. a buckle,
   I. the buckle having a first opening for passage therethrough of the circumferential belt first end,
   II. the buckle having a second opening for passage therethrough of the circumferential belt second end,
I. a first circumferential belt loop having a D-ring,
   I. the first circumferential belt loop having a D-ring being slidably attached to the circumferential belt, proximate to the circumferential belt second end,
   II. the first circumferential belt loop having a D-ring being attached to the first elastically adjustable shoulder strap second end,
J. a second circumferential belt loop having a D-ring,
   I. the second circumferential belt loop having a D-ring being slidably attached to the circumferential belt, proximate to the circumferential belt first end,
   II. the second circumferential belt loop having a D-ring being attached to the second elastically adjustable shoulder strap second end.

7. The rehabilitative shoulder support according to claim 6 further comprising:
A. a plurality of retainers
   I. the retainers each having a first end and a second end,
      a. the first end and second end being attached to the fourth elastic strap
B. an elastic adduction exercise strap,
   I. the elastic adduction exercise strap having a first end and a second end, II. the elastic adduction strap passing between the retainers and the fourth elastic strap,
III. the elastic adduction exercise strap first end being attached to strap attachment means
   a. the strap attachment means being permanently attached to the circumferential belt, proximate to the circumferential belt wide section,
IV. the elastic adduction exercise strap second end being attached to strap attachment means,
   a. the strap attachment means being permanently attached to the circumferential belt, proximate to the circumferential belt wide section.

8. The rehabilitative shoulder support according to claim 6 further comprising;
   A. a support strap,
      I. the support strap having a first end and a second end,
   B. a first support strap belt loop having a D-ring,
      I. the support strap first end being attached to the first support strap belt loop having a D-ring,
   C. a second support strap belt loop having a D-ring,
      I. the support strap second end being attached to the second support strap belt loop having a D-ring.

* * * * *